United States Patent [19]
Zey et al.

[11] Patent Number: 5,151,551
[45] Date of Patent: Sep. 29, 1992

[54] METHOD FOR PURIFICATION OF IBUPROFEN COMPRISING MIXTURES

[75] Inventors: Edward G. Zey; Thomas H. Shockley; Debra A. Ryan, all of Corpus Christi, Tex.; Gary L. Moss, Greer, S.C.

[73] Assignee: Hoechst Celanese Corporation, Somerville, N.J.

[21] Appl. No.: 579,427

[22] Filed: Sep. 6, 1990

[51] Int. Cl.$^5$ ............................................. C07C 51/42
[52] U.S. Cl. ....................................................... 562/494
[58] Field of Search .......................................... 562/494

[56] References Cited

U.S. PATENT DOCUMENTS

| 4,476,248 | 10/1984 | Gordon | 562/494 |
| 4,709,089 | 11/1987 | Shimizu | 562/494 |
| 4,981,995 | 1/1991 | Elango et al. | 562/406 |

FOREIGN PATENT DOCUMENTS

| 185041 | 8/1987 | Japan . |
| 294637 | 12/1987 | Japan . |
| 2-152945 | 6/1990 | Japan . |
| 079345 | 6/1982 | Romania . |

*Primary Examiner*—Paul J. Killos
*Attorney, Agent, or Firm*—Donald R. Cassady

[57] ABSTRACT

This invention pertains to a method of purifying ibuprofen-comprising reaction product mixtures. The method of purification is based on crystallization of ibuprofen from a hydrocarbon solvent and the discovery that there are impurity complexes in the ibuprofen-comprising reaction product mixtures which cannot be removed by crystallization from a hydrocarbon solvent.

The method of the invention includes at least one step in which the impurity complex in a first ibuprofen-comprising mixture is destabilized or broken up, followed by crystallization of the ibuprofen from a second solution or mixture comprising the first ibuprofen-comprising mixture, whereby the impurities which were previously complexed can then be removed from the ibuprofen by the crystallization of ibuprofen from a solvent.

21 Claims, 5 Drawing Sheets

FIG. 1
BASIC IBUPROFEN ROUTE
(WITHOUT HEAT TREATMENT)

FIG. 2
IBUPROFEN PURIFICATION ROUTE INVOLVING DISTILLATION FOLLOWED BY CRYSTALLIZATION

FIG. 3
IBUPROFEN PURIFICATION ROUTE WITHOUT XTAL PRIOR TO HEAT TREATMENT

FIG. 4

IBUPROFEN PURIFICATION ROUTE INCLUDING BOTH
MELT CRYSTALLIZATION AND CRYSTALLIZATION
FROM A SOLVENT

FIG. 5
IBUPROFEN PURIFICATION ROUTE WITH TWO CRYSTALLIZATIONS FROM SOLVENT AND HEAT TREATMENT

METHOD FOR PURIFICATION OF IBUPROFEN COMPRISING MIXTURES

BACKGROUND OF THE INVENTION

1. Field of the Invention

This invention relates to a method for purifying ibuprofen-comprising mixtures of the kind which are typically produced during a reaction process in which ibuprofen (2-(4'-isobutylphenyl)propionic acid) is formed.

2Background Art

Ibuprofen is a well-known nonsteroidal anti-inflammatory drug which has been converted from ethical, i.e., prescription, to over-the-counter status. The ibuprofen sold as a pharmaceutical must meet purity requirements specified by the U.S. Food and Drug Administration. In addition, the ibuprofen is typically sold over-the-counter in the form of tablets, and therefore it is advantageous to have the ibuprofen material be in a structural form which can be readily formed into tablets; typically tablet formation is facilitated when the average crystal size of the ibuprofen material ranges from about 15 microns to about 70 microns.

Ibuprofen-comprising mixtures which can be processed by the method of the present invention to yield purified ibuprofen which is capable of meeting U.S. Food and Drug Administration requirements include those produced by the methods such as the method described in U.S. patent Ser. No. 07/500,645, filed Mar. 28, 1990 U.S. Pat. No. 4,981,995. U.S. patent application Ser. No. 07/500,645 U.S. Pat. No. 4,981,995 is hereby incorporated by reference for purposes of providing background information helpful in understanding the present invention.

When ibuprofen is produced as described in U.S. patent application Ser. No. 07/500,645, U.S. Pat. No. 4,981,995 the process involves the carbonylation of 1-(4'-isobutylphenyl)ethanol (IBPE) with carbon monoxide while in contact with an acidic aqueous medium at a temperature of at least about 10° C. and a carbon monoxide pressure of at least about 500 psig, and in the presence of (1) a catalyst consisting essentially of a palladium compound in which the palladium has a valence of zero to 2 and is complexed with at least one acid stable monodentate phosphine ligand freely miscible with the organic phase of the reaction medium, the phosphorus:palladium mole ratio in said palladium compound and ligand being at least about 2:1 when the mole ratio of palladium to IBPE is such that palladium=1 and IBPE=10,000 or more; (2) dissociated hydrogen ions from an acid which is substantially completely ionizable in a dilute aqueous solution, such that the mole ratio of hydrogen ions to IBPE added to the reaction zone (H /IBPE) is at least about 0.15; and (3) dissociated halide ions such that the mole ratio of halide ions to IBPE added to the reaction zone (X$^-$/IBPE) is at least about 0.15.

The IBPE used to produce ibuprofen may be made by any of various means; preferably, however, the carbonylation reaction to produce ibuprofen is integrated with a method of producing IBPE from isobutylbenzene, wherein the latter compound is subjected to a Friedel-Crafts reaction with an acetylating agent to produce 4-isobutylacetophenone (IBAP) which is then reduced with hydrogen in the presence of a hydrogenation catalyst, or with a reducing agent containing available hydrogen, to obtain IBPE.

The crude reaction product mixture obtained in the above-described carbonylation reaction, contains ibuprofen at a concentration range of about 70% to about 98% by weight, and typically contains about 85%–95% by weight, having such undesirable impurities present as triphenylphosphine (TPP), triphenylphosphine oxide (TPPO), and organometallic compounds/complexes (typically organo-palladium compounds/complexes) which need to be removed.

Inorganic impurities typically present include hydrochloric acid, palladium-containing compounds and elemental palladium which also need to be removed.

Additional organic impurities, such as (but not limited to) 4-isobutylacetophenone, isobutylbenzene, 1-(4'isobutylethylbenzene, 1-(4'isobutylphenyl)ethyl chloride, 1-(4'-isobutylphenyl)ethanol, isopropylalcohol, isopropyl ester of ibuprofen, 3-(4'-isobutylphenyl)propionic acid and 2-(3'-isobutylphenyl)propionic acid are also typically present in the reaction product to be purified.

Several different methods of purification were initially attempted, including the most commonly used method of purification for similar reaction product materials, crystallization from a hydrocarbon solvent. However, it was discovered that such crystallization alone of the ibuprofen reaction product mixture was not sufficient to remove the TPP and TPPO. In fact, analytical data confirmed that very little if any TPP was removed by crystallization from hydrocarbon solvents.

In addition, crystallization from a hydrocarbon solvent did not remove metallic catalyst compounds/complexes from the reaction product mixture.

Melt crystallization and distillation of the ibuprofen reaction product mixture were also investigated as possible means of ibuprofen purification. Melt crystallization was investigated, but preliminary experiments indicated that due to the high viscosity of the crude ibuprofen and its individual constituents, melt crystallization is inefficient as an individual method of separation. For example, the TPP and TPPO combined concentration in the melt crystallized ibuprofen product was greater than the desired concentration of 10 ppm or less. Melt crystallization appears to be more expensive than distillation as a separation purification method. Although distillation appears to be a feasible method of purification, economic calculations show distillation, as an individual separation technique, to be expensive relative to crystallization from solvents; and, when distillation is used typically the 3-isomer is carried overhead with the ibuprofen (4-isomer), requiring subsequent processing for removal of the 3-isomer. The distillate ibuprofen product is in the form of oil which is typically cooled/solidified on a chilled drum and subsequently flaked. Conversion of the ibuprofen flakes to a particle size commonly used to manufacture tablets is difficult due to mechanical complexities.

Distillation, as a method of purifying an ibuprofen reaction product mixture, is disclosed in U.S. patent application Ser. No. 07/302,696, filed Jan. 25, 1989 now abandoned. This application disclosed a process for purifying 2-(4'-isobutylphenyl)propionic acid from a mixture, wherein the 2-(4'-isobutylphenyl)propionic acid is separated as a distillate fraction, by subjecting the mixture to a vacuum rectification.

SUMMARY OF THE INVENTION

The present invention pertains to a method of purification of ibuprofen-comprising mixtures, which purification comprises crystallization of ibuprofen from a hydrocarbon solvent. In accordance with the present invention, it has been discovered that, at least one complex comprising at least one ibuprofen molecule is present in the ibuprofen-comprising mixtures; this complex must be destabilized or broken up, whereby impurities which comprised the complex can be separated from the ibuprofen molecule, permiting ibuprofen of the desired purity to be obtained.

It appears that it is desirable to remove any uncomplexed acid present in the ibuprofen-comprising mixture prior to, or as a part of the steps necessary to destabilize or break up the at least one complex described above. In fact, removal of uncomplexed acid, in some instances, is sufficient in itself to destabilize the at least one complex. In other instances, it is necessary to heat treat the ibuprofen-comprising mixture, whereby uncomplexed acid is removed, complexed acid becomes uncomplexed and is removed, and the at least one complex is broken up.

To destabilize or break up the at least one complex between an ibuprofen molecule and reactants, by-products and/or catalysts which are present the ibuprofen-comprising reaction product mixture, it is necessary to substantially remove acidic compounds which are present in the reaction product mixture. The acidic compounds removed can be uncomplexed or complexed, but in any case it is necessary to remove substantially all of the uncomplexed acidic compounds which are initially present in the reaction product mixture, making these uncomplexed acidic compounds unavailable for complexing and shifting the equilibrium so that acidic compounds which are complexed tend to decomplex. In some instances, it may be feasible to directly decomplex acidic compounds present in the at least one complex, thus destabilizing or breaking up the complex comprising the ibuprofen molecule.

The acidic compounds can be removed by dissolving them in or complexing them with a medium which can be extracted or separated from the ibuprofen-comprising reaction product mixture. The acidic compounds can also be removed by heat treating the ibuprofen reactant product mixture to a temperature sufficient to destabilize or break up the at least one complex, while simultaneously providing a means for removing the acidic compounds as they become available from the destabilized or broken up complex.

One preferred embodiment of the present invention pertains to a method of purifying ibuprofen-comprising mixtures, which mixtures include or comprise halides and phosphorous-containing compounds. Another preferred embodiment of the present invention pertains to a method of purifying ibuprofen-comprising mixtures, which mixtures include or comprise a metallic catalyst compound and/or an acidic compound complex. Both of these preferred embodiments can be practiced using the same techniques to destabilize or break up complexes which form with an ibuprofen molecule.

The techniques used to destabilize or break up complexes which form with an ibuprofen molecule are disclosed in terms of specific process steps below.

One preferred embodiment of the present invention comprises the steps of:

(a) washing an ibuprofen-comprising first mixture, using at least one washing step, wherein the washing agent comprises water; and (b) crystallizing ibuprofen at least once from a second solution or mixture comprising the washed first ibuprofen mixture, and including at least one hydrocarbon solvent from which the ibuprofen is crystallized.

As an alternative, a second preferred embodiment comprises the steps of:

(a) heat treating a first solution or mixture comprising ibuprofen at a temperature sufficient to cause the decomposition of a complex which includes at least one ibuprofen molecule, whereby the decomposition products of such complex can subsequently be separated from the ibuprofen molecule; and (b) crystallizing ibuprofen at least once from a second solution or mixture comprising the heat treated first solution or mixture, and including at least one hydrocarbon solvent.

Another alternative preferred embodiment comprises the steps of:

(a) washing an ibuprofen-comprising first mixture, using at least one washing step, wherein the washing agent comprises water;

(b) heat treating a second solution or mixture comprising the washed ibuprofen-comprising first mixture at a temperature sufficient to cause the decomposition of a complex which includes at least one ibuprofen molecule, whereby the decomposition products of such complexes can subsequently be separated from the ibuprofen molecule; and (c) crystallizing ibuprofen at least once from a third solution or mixture which comprises the heat-treated second solution or mixture, and including at least one hydrocarbon solvent from which the ibuprofen is crystallized.

A potential alternative to a water wash step for removal of excess acid from the carbonylation mixture would be the use of azeotropy, wherein the azeotrope comprises the uncomplexed acid, water, and a hydrocarbon solvent. This potential technique is presently under investigation. Should use of azeotropy for the removal of uncomplexed acid prove economically feasible, the water wash step described herein can be replaced in the description of preferred embodiments throughout the method of the present invention by such azeotropy. In addition, depending on the temperature at which the azeotropy is carried out, the combination of a water wash step and a heat treatment step can be replaced by at least one azeotropy step.

There are numerous additional steps which can be used in the method of the present invention in addition to the critical combination of steps described in the preferred embodiments above. The discussion below describes purification of ibuprofen from an initial ibuprofen-comprising mixture using various auxiliary steps in combination with the critical steps, to provide one skilled in the art with an understanding of what is required to have a complete purification system. However, it will become immediately apparent that the number of auxiliary steps, and even the number of times one of the critical steps is repeated depends on the purity requirements for the finished product and the desired form of the finished product.

In one of the above-described preferred embodiments of the present invention, at least two water wash steps are conducted; a first water wash which is used to remove the bulk of the water soluble impurities from the ibuprofen-comprising mixture (typically the reaction mixture), followed by a second water wash containing a base, which base is reacted with any uncomplexed and complexed acid from the ibuprofen-comprising mixture (such as the uncomplexed acid remaining after the above-described carbonylation step disclosed in U.S. patent application Ser. No. 07/500,645) U.S. Pat. No. 4,981,995 which remains in the crude ibuprofen-comprising mixture, even after the first water wash. A third water wash can be used to ensure that the salts formed from reaction of the uncomplexed acid with the base are removed.

These water washing steps are known to remove uncomplexed and complexed acid from the ibuprofen-comprising mixture, which, in some instances, makes it possible upon subsequent crystallization of ibuprofen from a solution or mixture comprising a hydrocarbon solvent, to obtain ibuprofen which meets pharmaceutical requirements and standards for purity.

In another preferred embodiment of the invention, a solution or mixture comprising ibuprofen is heat treated to cause the decomposition or decomplexing of the at least one complex previously described, which complex is typically intermingled with and is believed to be complexed with at least one ibuprofen molecule, which complex is detrimental in view of intended applications for the ibuprofen, and which complex is not removed upon crystallization of the ibuprofen from a solution of ibuprofen.

Heat treatment of a solution or mixture comprising ibuprofen accomplishes several desirable tasks: (1) The breaking down of a complex to decomposition products which can be separated from the ibuprofen upon crystallization of the ibuprofen from a solvent. (2) Provision of a method for the removal of complex components from the ibuprofen-containing solution or mixture, when the heat treatment temperature is sufficient to cause both decomposition of the complex, and formation of a gas which comprises a complex component and which gas can be withdrawn from the heat treatment process. Also, any residual, volatile compounds which contain potential complex components would typically be vaporized during the heat treatment process. (3) Provision of a method for precipitation of non-volatile catalyst complexes and decomposition products thereof from an ibuprofen-comprising solution or mixture, when the heat treatment conditions are adequate to destabilize the catalyst compound within the solution, thereby permitting precipitation. Separation techniques such as filtration or centrifugation can then be used to remove precipitants from a solution comprising ibuprofen.

Crystallization of ibuprofen from a solution or mixture comprising at least one hydrocarbon solvent (from which ibuprofen can be crystallized) can be repeated a number of times to provide ibuprofen of increased purity. The number of crystallization steps necessary depends on the initial composition of the ibuprofen-comprising mixture to be purified, the degree of purification achieved upon a single crystallization step and the required purity of the final, purified ibuprofen product.

To summarize several of the preferred embodiments of the present invention:

A first, preferred embodiment of the present method for purification of an ibuprofen-comprising mixture comprises the steps of:

(a) at least one water washing of an ibuprofen-comprising first mixture; and, (b) at least one crystallization of ibuprofen from a second solution or mixture comprising the first mixture, and including at least one hydrocarbon solvent from which the ibuprofen is crystallized.

A second, preferred embodiment of the present method for purification of an ibuprofen-comprising mixture comprises the steps of:

(a) heat treating a first solution or mixture comprising ibuprofen at a temperature sufficient to cause the decomposition of a complex which includes at least one ibuprofen molecule, whereby the decomposition products of such complex can subsequently be separated from the ibuprofen molecule; and (b) crystallizing ibuprofen at least once from a second solution or mixture comprising the heat treated first solution or mixture, and including at least one hydrocarbon solvent.

A third, preferred embodiment of the present method for purification of an ibuprofen-containing mixture comprises the steps of:

(a) at least one water washing of an ibuprofen-comprising first mixture;

(b) heat treatment of a second solution or mixture comprising the washed first ibuprofen-containing mixture at a temperature sufficient to cause the decomposition or decomplexing of the at least one complex which is present in the mixture; and, (c) at least one crystallization of ibuprofen from a third solution or mixture comprising the heat treated second solution or mixture and including at least one hydrocarbon solvent from which the ibuprofen is crystallized;

A fourth, preferred embodiment of the present method for purification of an ibuprofen-comprising mixture comprises the steps of:

(a) at least one water washing of an ibuprofen-comprising first mixture;

(b) melt crystallization of a second solution or mixture comprising the washed first ibuprofen-comprising mixture; and, (c) at least one crystallization of ibuprofen from a third solution or mixture comprising the melt crystallized second solution or mixture, and including at least one hydrocarbon solvent from which the ibuprofen is crystallized.

A fifth, preferred embodiment of the present method for purification of an ibuprofen-comprising mixture comprises the steps of:

(a) at least one water washing of an ibuprofen-comprising first mixture;

(b) a first crystallization of ibuprofen from a second solution or mixture comprising the washed first mixture, and including at least one hydrocarbon solvent from which the ibuprofen is crystallized;

(c) heat treatment of the crystallized ibuprofen or a third solution or mixture comprising the crystallized ibuprofen, at a temperature sufficient to cause the decomposition of at least one complex which includes at least one ibuprofen molecule, whereby the decomposition products of such complexes can subsequently be separated by crystallization from the ibuprofen molecule; and, (d) a second crystallization of ibuprofen from a fourth solution or mixture comprising the heat treated third solution or mixture, and including at least one hydrocarbon solvent from which the ibuprofen is crystallized.

Heat treatment steps such as (a) in the second preferred embodiment described above, (b) in the third preferred embodiment described above, and (c) in the fifth preferred embodiment described above also provide a means of precipitating metallic catalyst compounds/complexes from an ibuprofen-comprising solution.

Each of the preferred embodiments disclosed above can include solid/liquid separation steps, and a drying step following the last crystallization, whereby the residual solvent remaining on the ibuprofen crystals is removed.

Each of the preferred embodiments described above can be carried out in a series of batch-type steps, in a continuous manner, and in a semi-continuous manner. One skilled in the art can arrange the unit operations within the method of the invention as desired in view of process economics.

BRIEF DESCRIPTION OF THE DRAWINGS

Note that in all of the proposed methods, there are additional non-critical but likely to be used steps, such as filtering, drying, and recycling steps in which particular sidestreams are further processed to provide for additional recovery of ibuprofen product and to provide for the return of solvents and other recyclable materials to the main process stream.

DETAILED DESCRIPTION OF THE PREFERRED EMBODIMENTS

The present requirements for pharmaceutical grade ibuprofen under U.S. and British pharmacopoeia define a product having an assay greater than 98.5% by weight ibuprofen by acid titration. Appearance is to be white or nearly white. The ibuprofen compound melting point must range between 75.0° C. and 77.5° C. Residue upon ignition is required to be less than 0.1% by weight and heavy metals content must be less than 0.001% by weight. There are also infrared and ultraviolet standard scans which must be matched by the product ibuprofen. Total organic impurities, measured by HPLC, should total no more than 1.0% by weight, wherein no single organic impurity exceeds 0.3% by weight.

There are also generally accepted commercial standards for the ibuprofen product. Under these standards, chloride content of the ibuprofen product (wet chemistry reaction with silver nitrate) should not reveal any opalescence due to silver chloride formation. Chloride content as determined by X-Ray analysis should be less than 10 ppm. Total phosphorus as determined by wet chemical photometric assay using the phosphomolybdate blue method should be less than 10 ppm, and preferably less than 1 ppm. The total phosphorus content includes triphenylphosphine (TPP) and triphenylphosphine oxide (TPPO). TPP and TPPO can be determined individually using a Hewlett-Packard 5890 capillary gas chromatograph with a flame photometric detector, to evaluate a 10% by weight solution of the ibuprofen product in acetonitrile, if desired; this capillary method can also be used to measure trace amounts of other phosphorous organic impurities, which are typically included in calculating the 10 ppm or less. For processes wherein a metallic catalyst content (such as palladium) is also monitored, the desired residual metal content in the ibuprofen product is less than 5 ppm when measured by inductively coupled plasma or atomic absorption spectrophotometry.

In view of the intended use of ibuprofen as an ingested pharmaceutical, which has engendered particular requirements and standards, it becomes readily apparent that purification of an ibuprofen-comprising reation mixture is of crital importance.

When the ibuprofen product is to be sold in tablet form, it is desirable to provide the ibuprofen in the form of dried crystals having a mean particle diameter falling in the range from about 15 to about 70 micrometers. The preferred mean particle diameter for dried crystals ranges from about 15 to about 60 micrometers.

Table I below shows the composition of several crude ibuprofen reaction product mixtures which are typical of the kind of ibuprofen-comprising mixtures which are produced by a synthesis method including carbonylation, of the kind described previously. Such mixtures can be purified so they meet current U.S. and British Pharmacopoeial Standards and commercial standards for ibuprofen using the purification method of the present invention. The Table I mixture descriptions are not intended to place limitations upon the kind of ibuprofen-containing mixtures which can be purified by the method of the present invention, but are intended to provide one skilled in the art with examples which are sufficiently informative that one skilled in the art can apply the method of the present invention to other ibuprofen-comprising mixtures.

TABLE I

TYPICAL CRUDE IBUPROFEN-COMPRISING MIXTURES

| Mixture Number | IBPCL (wt %) | 3IBU (wt %) | IBU (wt %) | LIN ISO (wt %) | TPP ppm or (%) | TPPO (ppm) | OTHER P (ppm) | $H_2O$ (wt %) | OTHER ORGANIC IMPURITIES (wt %) |
|---|---|---|---|---|---|---|---|---|---|
| 1. | 0.11 | 1.8 | 85.9 | 0.8 | 189 | 127 | 16 | 0.75 | >7.6 |
| 2. | 0.10 | 1.6 | 86.7 | 0.5 | 417 | 108 | 34 | 2.39 | >7.1 |
| 3. | 0.11 | 1.9 | 86.4 | 0.8 | 205 | 132 | 23 | 0.73 | >9.0 |
| 4. | 0.12 | 1.8 | 93.7 | 0.6 | 37 | 60 | 5 | NDT | >2.0 |
| 5. | 0.57 | 1.3 | 87.0 | 1.1 | 0.04 (%) | ND | ND | NDT | >5.1 |
| 6. | 0.66 | 1.3 | 89.8 | 1.2 | 0.07 (%) | ND | ND | NDT | >6.1 |
| 7. | NDT | ND | 78.9 | 6.6 | 0.51 (%) | NDT | NDT | NDT | >11.3 |

TABLE I-continued

TYPICAL CRUDE IBUPROFEN-COMPRISING MIXTURES

| Mixture Number | IBPCL (wt %) | 3IBU (wt %) | IBU (wt %) | LIN ISO (wt %) | TPP ppm or (%) | TPPO (ppm) | OTHER P (ppm) | $H_2O$ (wt %) | OTHER ORGANIC IMPURITIES (wt %) |
|---|---|---|---|---|---|---|---|---|---|
| 8. | NDT | ND | 79.9 | 5.2 | 0.52 (%) | NDT | NDT | NDT | >13.6 |

ND = Not Detected
NDT = Not Determined
IBPCl = 1-(4'Isobutylphenyl)chloroethane
3IBU = 1-(3'-isobutylphenyl)propionic acid
IBU = Ibuprofen
LIN ISO = Linear isomer
TPP = Triphenylphosphine
TPPO = Triphenylphosphine oxide
OTHER P = Other phosphorous compounds
$H_2O$ = Water The ibuprofen-comprising mixtures described in Table I comprise organic halogen-containing compounds which can decompose to hydrogen chloride. The ibuprofen-comprising mixture additionally contains complexes which can decompose to produce both halogen-containing and phosphorus-containing compounds. Initial attempts to reduce the halogen-containing and phosphorus-containing compounds to acceptably low concentrations in the ibuprofen product via crystallization from a solvent failed. Applicants then discovered that the halogen-containing and phosphorus containing compounds were present in the form of a complex in the ibuprofen-comprising mixtures. The complexes are believed to be formed between the halogen-containing compounds, the phosphorus-containing compounds, and the ibuprofen itself and could not be removed from the ibuprofen by crystallization of the ibuprofen from a solvent.

To aid in the subsequent removal of the halogen and phosphorus-containing compounds and complexes described above, applicants used a water wash to solvate and remove the halogen-containing acidic compounds, which in some instances resulted in decomposition of the complex itself, permitting subsequent purification of the ibuprofen via crystallization of the washed ibuprofen-containing mixture from a solvent. Use of a water wash containing a base, which base reacts with the halogen-containing acidic compounds to form a water soluble reaction product, makes the water wash more effective in reduction of the halogen-containing acidic compounds.

Related to the crude, ibuprofen-comprising mixture produced by the synthesis method described in U.S. patent application Ser. No. 07/500,645, it was discovered that, in purification, it is critical to remove residual acidic compounds. Without removal of such acidic compounds (HCl for example) which are used in the carbonylation step, complexes are formed with phosphorus-containing compounds and the ibuprofen. Such complexes include, for example, a triphenylphosphonium salt-HCl-ibuprofen complex, which complex is believed to have the structure:

A complex of the type shown above is believed to be formed when triphenylphosphonium chloride salt complexes with acid compounds, such as HCl, and with the ibuprofen product. Laboratory data indicate the triphenylphosphonium chloride salt can be removed from ibuprofen by crystallization from a hydrocarbon solvent if a strong acid is not present. However, once the acid-comprising complex forms, it is extremely difficult, if not impossible, to remove the complex from the ibuprofen product by crystallization from a solvent.

Use of at least one water wash (wherein the water wash can contain a base to provide a more effective removal) to remove uncomplexed acidic compounds from the ibuprofen-containing mixture, leading to removal of the halogen-containing acid (or other strong acid such as sulfuric acid) present as part of the complex, results in the production of an ibuprofen mixture from which the phosphorous and halogen-containing compounds can be removed from the ibuprofen via crystallization from a solvent.

Applicants discovered that a reduction in the amount of TPP, TPPO, and residual halogen or halogen containing compounds in the purified ibuprofen can also be obtained by heat treating the ibuprofen-comprising mixture. The heat treatment decomposes the ibuprofen-halogen-phosphorus compound complex so the component parts of the complex can be separated. Some of the component parts can be removed from the ibuprofen-comprising mixture as a gas (HCl for example). Other component parts can be separated from the ibuprofen upon crystallization of the ibuprofen from a hydrocarbon solvent.

The heat-treatment was discovered to provide an additional benefit in that it caused the precipitation of elemental palladium from the ibuprofen-comprising mixture. Laboratory data indicate there is likely to be a second complex comprising a palladium compound, acid and ibuprofen. The second complex behaves in a manner similar to that for the complex described above upon water washing. In addition, this second complex is decomposed on heat treatment, displacing the acid, precipitating a palladium-comprising compound, and affording a product mixture which can be purified by crystallization of the ibuprofen from a hydrocarbon solvent. The precipitated elemental palladium is typically removed by filtration of the heat-treated ibuprofen-comprising mixture prior to crystallization of the ibuprofen.

The method of the present invention is further illustrated using FIGS. 1-5 previously discussed briefly herein.

Figure 1:
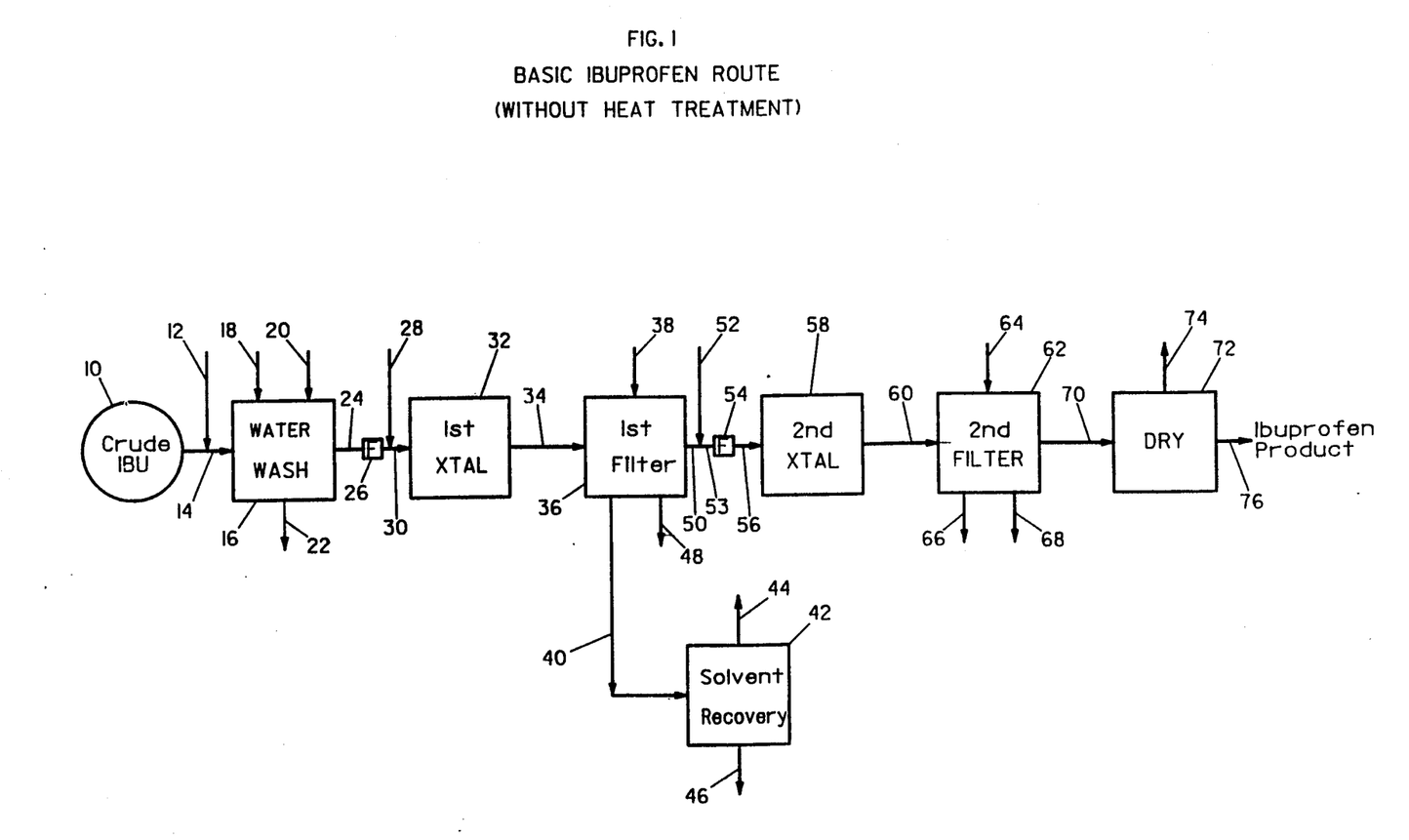
FIG. 1 shows a schematic of a basic purification method, including at least one water wash, at least one (and preferably two) crystallization of ibuprofen from a hydrocarbon solvent, and a drying step to remove residual hydrocarbon solvent from the ibuprofen.

FIG. 1 shows a schematic wherein crude ibuprofen-comprising reaction mixture (crude IBU) 10 is water washed 16 at least once to remove chloride-containing compounds, excess HCl, and the complexed HCl as discussed above from crude IBU 10. The water washed mixture 24 is subsequently crystallized from a solvent twice (32 and 58) to provide the purified ibuprofen product 76. Crude IBU 10 must be melted, ie. heated to a temperature of about 60° C. (depending on the exact composition of the mixture) to ensure that the mixture is a liquid entering the purification process. To the heated mixture is added a hydrocarbon solvent (preferably a saturated hydrocarbon solvent) 12 for the ibuprofen is added to the crude IBU 10. The hydrocarbon solvent 12 is used to prevent the formation of an emulsion when the crude IBU 10 is water washed 16 and to provide a less viscous mixture 14. Typically, the amount of hydrocarbon solvent 12 added is such that the concentration of crude IBU 10 in the crude IBU-hydrocarbon solvent solution 14 ranges from about 10% to about 60% by weight. Examples of saturated hydrocarbon solvents which are preferred include, but are not limited to, hexane, heptane, octane, cyclohexane, and mixtures thereof. Unsaturated hydrocarbon solvents such as, but not limited to, 1-hexene and toluene, can also be used. Solvents which boil at higher temperatures are less desirable because they are difficult to remove from ibuprofen product during drying step 72. Thus, a solvent like hexane is preferred over a solvent like toluene for use in the method of the present invention. Solubility of the ibuprofen product in the solvent is also important, with lower solubility of the ibuprofen being preferred. Thus, a solvent like heptane or hexane is preferred over a solvent like toluene.

In the water wash step 16, at least one water wash is conducted, wherein water 18 and/or a water/base solution 20 is contacted with the crude IBU-hydrocarbon solvent solution 14. After the contacting, the crude IBU-hydrocarbon solvent solution 24 is separated from the wash water 22 by phasing and draining. The wash water 22 may be filtered, neutralized, and the resulting salt solution may be discarded. The crude IBU-comprising, mixture-saturated hydrocarbon solvent solution 24 may then be filtered at step 26 to remove suspended solids (the suspended solids are typically comprised of precipitated palladium and polymeric materials) from solution 24.

The water washed, filtered IBU-comprising hydrocarbon solution 30 then passes to the first solvent crystallization 32. If desired, additional hydrocarbon solvent 28 can be added to the IBU-comprising hydrocarbon solution. Typically additional solvent 28 is added to adjust the composition of the IBU-comprising hydrocarbon solution 30 so that the developing viscosity of the first crystallization slurry (which forms in step 32) promotes satisfactory agitation of the slurry and improved crystallization efficiency during crystallization. Typically the concentration of IBU in hydrocarbon solution 30 ranges from about 10% by weight to about 60% by weight. The temperature of solution 30 is adjusted so that it ranges from about 55° C. to about 110° C., depending on the hydrocarbon solvent used. Solution 30 is then cooled in first crystallization step 32 at a rate ranging from about 0.01° C./min to about 4.0° C./min, until crystals begin to form. The cooling rate is then reduced to range from about 0.02° C./min to about 1.0° C./min to a temperature ranging from about 30° C. to about −5° C. (depending on the solvent used and the concentration of IBU in the solution), whereby a first crystallization slurry 34 containing IBU crystals is obtained.

First crystallization slurry 34 is then filtered cold (at the −5° C. to 30° C. temperature discussed above) in first filtration step 36. First filtration 36 produces IBU solids 50 and a first mother liquor solution 40. First mother liquor solution 40 is typically sent to a solvent recovery system 42, such as a distillation column, from which solvent(s) 44 are recovered and heavy ends (residue) 46 are obtained. The IBU solids resulting from the first filtration may be washed with additional cold hydrocarbon solvent 38 to produce washed crystals 50, while solvent wash (liquor) 48 can be recycled to positions such as solvent addition 12 or 28, to prevent IBU loss.

Washed crystals 50 can then be melted and combined with sufficient warm hydrocarbon solvent 52, or can be directly dissolved in warm hydrocarbon solvent 52 to prepare a diluted IBU-comprising solution 53 which is subsequently heated to a temperature ranging from about 55° C. to about 110° C. Optionally solution 53 can be filtered 54 to remove any suspended solids. Filtered IBU-comprising solution 56 typically contains from about 10% to about 60% by weight IBU. IBU-containing solution 56 is then cooled in second crystallization step 58 at a rate ranging from about 0.1° C./min to about 2° C./min until crystals begin to form. Solution 56 is subsequently additionally cooled at a rate ranging from about 0.02° C./min to about 0.1° C./min to a temperature ranging from about 10° C. to about −5° C., to produce a second crystallization slurry 60 containing IBU crystals. The IBU crystals obtained range in size from about 15 micron effective average particle diameter to about 70 micron effective average particle diameter.

Second crystallization slurry 60 is then filtered in second filtering step 62. Second mother liquor 66 can then be recycled to streams such as 12, 28, or 38. The filtered IBU-crystalline solids can then be washed with hydrocarbon solvent 64, with wash solvent 68 being recycled to solvent addition points such as 12, 28, 38, or 52.

Washed IBU crystalline solids 70 are then sent on to drying step 72, wherein residual hydrocarbon solvents 74 are removed. Typically, drying is conducted over a temperature range from about 40° C. to about 60° C. at a pressure ranging from about 250 mm Hg to about 2 mm Hg vacuum for a time period ranging from about 30 min to about 30 hours (depending on whether a dynamic or static drying operation is used). Hydrocarbon solvent 74 removed during drying may be recycled to solvent addition points 12, 28, 38, 52, or 64. The dried IBU product 76 meets the product specifications requirements previously described.

Example 1 below is substantially a specific example of a laboratory execution of the process shown schematically in FIG. 1, and described above.

EXAMPLE 1

A 700 g sample of crude ibuprofen mixture, containing about 90% by weight IBU was melted in a beaker on a hot plate a temperature of about 75° C. The melted mixture was combined with about 554 g of warm hexane, to produce a solution composed of about 56 wt % of the above crude ibuprofen mixture.

This solution was washed at a temperature of about 60° C. using about 1,050 ml of 60° C. deionized water. The solution was contained in a temperature-controlled, nitrogen atmosphere blanketed vessel, and the 60° C. deionized water was charged to the vessel while the solution was under agitation. The wash time period (during which the solution was under agitation) was about 30 minutes. The agitation was discontinued and the IBU/hydrocarbon solution phase separated from the water; the water layer was decanted. The pH of the water layer was determined. The water washing step was repeated, typically two to three times, until the pH of the decanted water layer was equal to or greater than about 2.9. Suspended solids were frequently observed in the interface between the IBU/hydrocarbon-comprising solution and the water layer. These solids were discarded along with the water wash. In engineering practice, the IBU/hydrocarbon-comprising solution may be filtered to remove such solids.

One thousand and seventy-nine (1079)g of warm hexane was then added to the filtered IBU/hydrocarbon-comprising solution to adjust the IBU concentration in the solution to about 30% by weight. The IBU/-hydrocarbon-comprising solution temperature was then adjusted to about 60° C. Subsequently, the solution was cooled at a rate of about 0.3° C./min to about 25° C., was held at 25° C. for about one hour, and was then cooled at a rate of about 0.3° C./min to about 5° C. The cooled solution produced a first slurry of IBU crystals in a hydrocarbon-comprising mixture.

The slurry described above was then filtered cold at about 10° C. under vacuum (about 252 mm Hg) to produce first crystalline solids and a first mother liquor solution. The vacuum was discontinued and the first crystalline solids were slurried with about 1,400 ml of 5° C. hexane. Then the vacuum was reconnected and the wash hexane drawn off the crystallized solids.

The first mother liquor was fed to a hexane recovery column for solvent recovery by distillation. In a production process, the wash hexane would typically be recycled. In this laboratory process, the wash hexane was discarded.

The first crystalline solids (crystallized IBU-comprising residual impurities) were then melted as previously described and combined with sufficient warm hexane to prepare a solution comprising 40 wt % of first crystalline solids. In engineering practice, any nondissolved solids observed in the solution at 60° C. can be removed by filtration.

The 40 wt % solution was then cooled from about 60° C. to about 5° C. over a time period of about 6 to 8 hours, at a relatively constant cooling rate to produce a second slurry of IBU crystals in a hydrocarbon-comprising mixture. This second slurry was filtered cold, at about 10° C., under vacuum (about 252 mm Hg). The filtered second crystalline solids were washed using 5° C. hexane, as previously described.

The filtered second crystalline solids were dried on a tray in a vacuum oven at about 50° C. under about 49 mm Hg vacuum over night. The composition of the second crystalline solids obtained was analyzed to be:

| Analyzed Composition of Second Solids | |
|---|---|
| IBU Assay (by titration) | 99.7% |
| Organic Impurities (HPLC) | 0.15% |
| Total TPP and TPPO | 3.0 ppm |
| Elemental Palladium (atomic absorption) | 2.6 ppm |
| Chloride (by X-ray) | 58 ppm |

Figure 2:
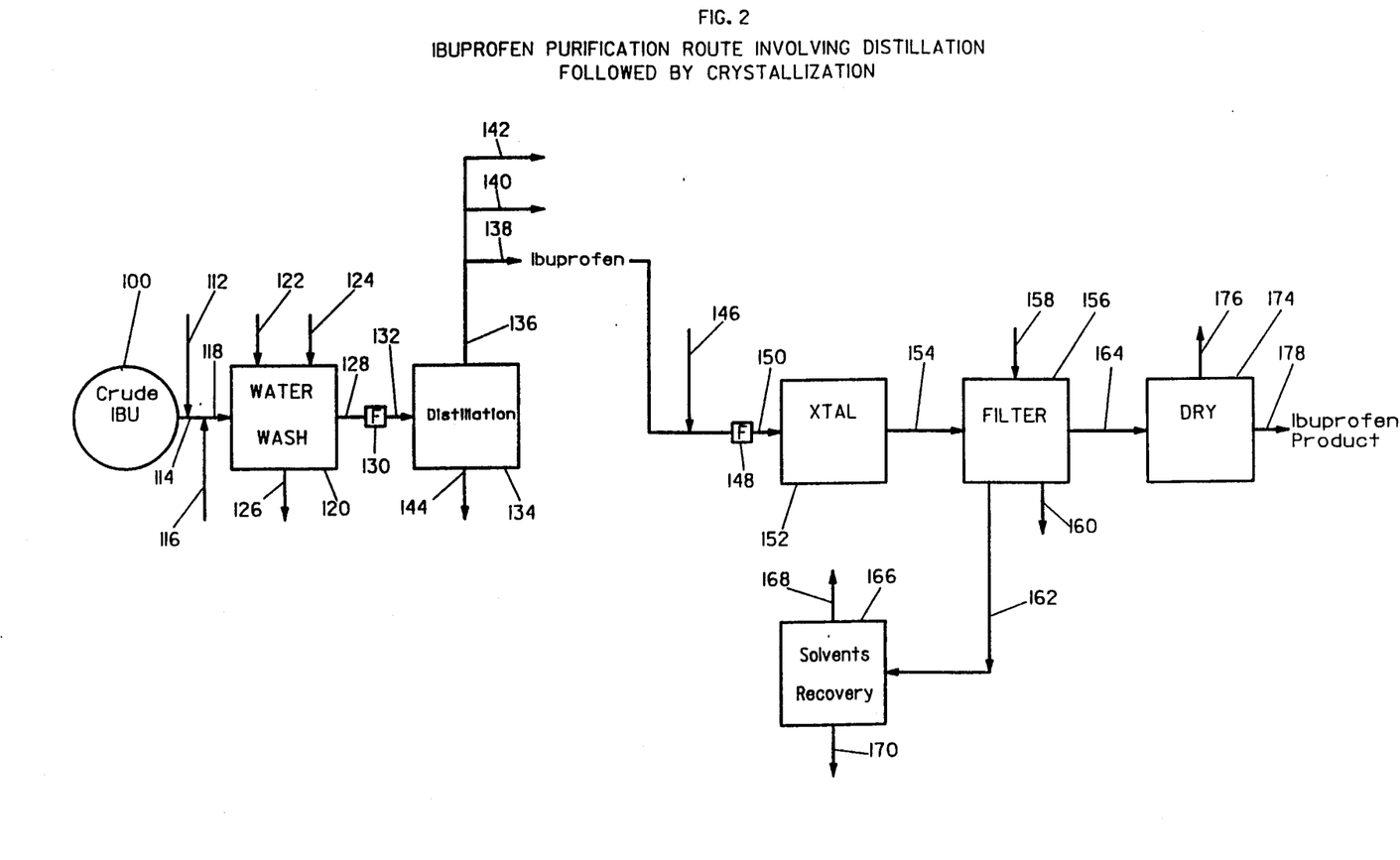
FIG. 2 shows a schematic of a another purification method including at least one water wash, a heat treatment step, in the form of distillation, at least one crystallization, and a drying step.

FIG. 2 shows a schematic wherein crude ibuprofen-comprising comprising reaction mixture (crude IBU) 100 is water washed at least once 120, heat treated/distilled 134, and then solvent crystallized 152 to provide the purified ibuprofen product 178. Again, the crude IBU 100 is melted, ie. heated to a temperature of about 60° C., to ensure that the mixture is a liquid entering the purification process. To the heated mixture is added a hydrocarbon solvent 112, to provide a less viscous mixture 114 comprising about 10% by weight to about 60% by weight crude IBU mixture 100. It is also possible to add recycled solvent 116 recovered from solvent recovery 166 at this point. The recycled solvent 116 can be added in addition to hydrocarbon solvent 112 or in place of such solvent, depending on the overall material balance desired. The resulting mixture 118 is then sent on to water wash step 120 wherein at least one water wash is used to remove chloride-containing compounds, excess HCl, and the complexed HCl previously discussed, from crude IBU 100. The diluted mixture 118 typically is comprised of about 10 wt % to about 60 wt % of crude IBU 100. This diluted mixture 118 is contacted at least once with water 122 and/or a water-base solution 124. After contacting mixture 118 with water 122 and/or 124, the mixture comprising IBU and hydrocarbon solvent 128 is separated from the wash water 126 by phasing and subsequent draining. Any number of wash steps can be used. Typically water washing is carried out until the pH of the decanted (drained) water layer is 2.9 or greater. Contacted wash water 126 may be filtered, neutralized, and the resulting salt solution may be discarded, recycled or reused in other plant operations. The IBU-comprising mixture 128 may then be filtered at step 130 to remove suspended solids from mixture 128.

The water washed, filtered IBU-comprising mixture 132 then passes to a heat treatment/distillation step 134.

Ibuprofen (IBU) separates from a solution or mixture as a distillate fraction at about 180° C.–200° C. at 10 mm Hg vacuum. It was discovered that the complex (such as a complex including a halogen-phosphorus-containing containing compound, halogen-containing acid, and at least one ibuprofen molecule) was destabilized or broken at such temperatures at 10 mm Hg vacuum. At about 0.6 mm Hg vacuum, the ibuprofen separates from a solution or mixture as a distillate fraction at about 130° C.; it was discovered that the complex had been broken by this temperature. As the complex was broken, the use of a vacuum to maintain a low pressure in the distillation unit assisted by pulling liberated HCl away from the IBU-comprising liquid mixture, which forced the equilibrium in the liquid mixture toward a reduced amount of the complex. The distillation 134 can be carried out at a temperature convenient in view of the hydrocarbon solvent(s) present. There are several fractions of IBU-comprising mixture 136 which can be separated in distillation 134. Typically the lowest temperature boiling component will be the hydrocarbon solvent(s) fraction 142. Ibuprofen light ends 140, such as isobutylethylbenzene and isobutylacetophenone, would comprise another fraction to be separated in distillation 134. The distillation can be carried out using a method of the kind described in U.S. patent application Ser. No. 07/302,969. The ibuprofen product fraction 138 is sent on to the next processing step. The heavy ends or residue 144 from the distillation can be further processed prior to discarding or recovery for use elsewhere.

To ibuprofen product fraction 138 hydrocarbon solvent(s) 146 is added to produce a solution from which the ibuprofen product can be crystallized in crystallization step 152. After addition of solvent(s) 146 the ibuprofen-comprising solution may be filtered 148 to remove any heavy ends materials entrained in ibuprofen product fraction 138. Entrained materials typically comprise palladium and polymer components. The filtered mixture or solution 150 is then further processed in crystallization step 152. Typically the concentration of IBU in solution 150 ranges from about 10% by weight to about 60% by weight. The temperature of solution or mixture 150 is adjusted so that it ranges from about 55° C. to about 110° C. depending on the hydrocarbon solvent used. The solution or mixture 150 is then cooled in crystallization step 152 at a rate ranging from about 0.01° C./min to about 0.6° C./min, until crystals begin to form, and subsequently at a rate ranging from about 0.02° C./min to about 0.1° C./min until a temperature ranging from about 10° C. to about −5° C. is obtained whereby a slurry 154 containing IBU crystals is obtained.

Crystallization slurry 154 is then filtered cold, as previously described, in filtration step 156. Wash solvent 158 (also cold) may be used to wash the filtered crystals. A first mother liquor 162 is typically sent to solvent recovery 166, such as a distillation column, from which solvent(s) 168 are recovered and heavy ends (residue 170 are obtained. Wash solvent 160 can be recycled in the process, and is typically fed back into the process at solvent addition point 116 or at alternative addition point 146. The IBU solids 164 resulting from filtration step 156 can then be dried in drying step 174 or can be remelted and further processed for purification.

Typically drying 174 is conducted over the temperature range necessary to remove hydrocarbon solvent(s) 176. The temperature and pressure conditions used during drying are provided in the drying step description of FIG. 1. Hydrocarbon solvents 176 may be recycled to solvent addition points such as 112, 146, or 158. Dried IBU product 176 meets the product specification requirements previously described.

Example 2 below is a specific example of a laboratory execution of the process shown schematically in FIG. 2, and described above.

EXAMPLE 2

A 700 gm sample of crude ibuprofen-comprising reaction product mixture was melted in a flask over a heated surface, combined with 554 gm of warm heptane (56 wt/wt %), and heated to 70° C.

The ibuprofen-comprising mixture-heptane solution was washed at a temperature of about 70° C. using about 1050 ml of 70° C. deionized water. The solution was contained in a temperature-controlled and nitrogen-atmosphere-blanked vessel and was under agitation, as previously described. The wash time period was about 30 minutes. The agitation was discontinued, the water layer was decanted, and the pH of the water layer was determined. The water washing step was repeated (usually two to three times) until the pH of decanted water layer was equal to or greater than 2.9. If suspended solids were noticed in the resulting heptane layer, the solution was filtered to remove such solids.

The washed heptane solution from the preceding step was vacuum flashed at about 50° C. at about 200 mm Hg. to remove heptane solvent. The resulting residue containing the ibuprofen product was then charged to a vacuum distillation column (50 mm×1.2 m) packed with Goodloe packing. After a light-ends fraction was removed at temperatures from about 20° C. to about 130° C. at 0.3–0.7 mm Hg, the ibuprofen product was distilled at 130°–134° C. under 0.3–0.7 mm Hg. The following analyses illustrate the effectiveness of this distillation step:

| Analysis | Crude Ibuprofen | Distilled Ibuprofen |
| --- | --- | --- |
| Ibuprofen Assay | 88.6% | 97.4% |
| 3-IBU (*) | 1.9% | 1.6% |
| Other Organic Impurities (GC) | 5.6% | 0.2% |
| Total TPP + TPPO | 499 ppm | 0.5 ppm |

(*) 3-IBU is defined as 2-(3'-Isobutylphenyl)propionic Acid.

Crystallization from a solvent was carried out as follows. The distilled ibuprofen product from the preceding step was combined with sufficient warm heptane to prepare a 25 wt/wt % solution and was heated to 70° C. If suspended solids were noted during dissolution, the mixture was filtered to remove such solids. The heated solution mentioned above was cooled for 30 minutes in an ice bath to produce a crystal-comprising slurry.

A second filtration was then carried out. The crystal-comprising slurry generated in the preceding step was filtered cold at temperatures ranging from 3° C. to 10° C., under a vacuum of about 50 mm Hg. The resulting solids were washed with 0° C. heptane (200 ml heptane wash per 100 gm of ibuprofen-comprising mixture). In a production process, such as that shown in FIG. 2, the mother liquor and wash solvent can be recycled to minimize solvent (such as heptane) loss.

Drying of the filtered and washed solids obtained in the previous step was carried out at about 50° C. under 50 mm Hg vacuum overnight. The solids thus obtained were analyzed to be as follows:

| | |
| --- | --- |
| Ibuprofen Assay | 99.8% |
| 3-IBU | 0.15% |
| Other Organic Impurities (GC) | Not Determined |
| Total TPP + TPPO | 0.39 ppm |
| Chloride | <10 ppm |

Figure 3:
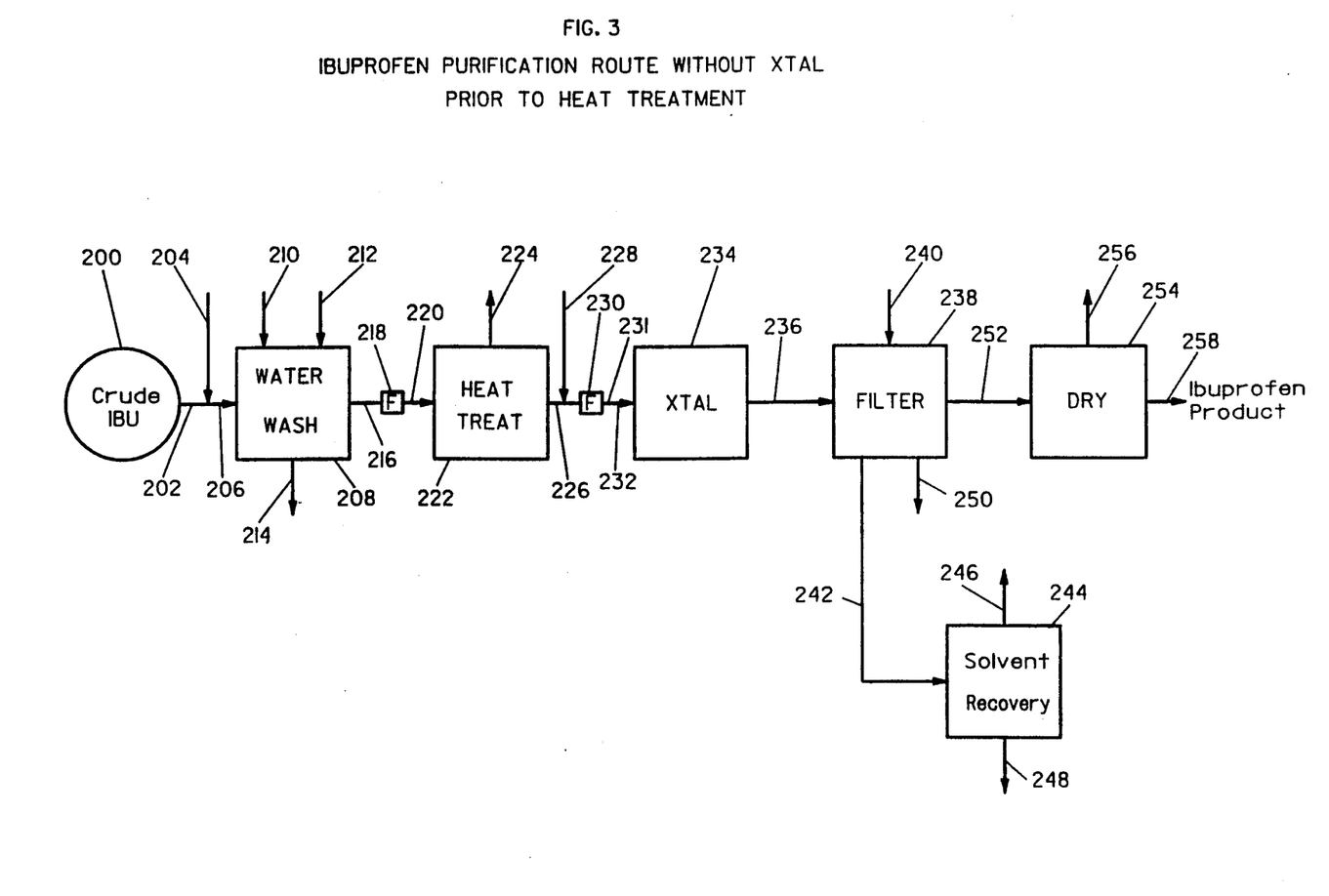
FIG. 3 shows a schematic of substantially the same method as that shown in FIG. 2, except that the heat treatment step does not comprise a distillation wherein the ibuprofen is taken off as a distillate fraction.

FIG. 3 shows a schematic of a purification process wherein the crude ibuprofen-comprising reaction mixture 200 is water washed at least once 208; heat treated 222 by a method which does not provide distillation (of a series of fractions); crystallized from a solvent 234; filtered 238; and typically dried 254 to remove residual solvent. The crude ibuprofen-comprising reaction mixture 200 is melted as previously described, and to the melt 202 is added a hydrocarbon solvent(s) 204, to provide a less viscous mixture 206, as previously described. Mixture 206 is then water washed 208 at least once to remove complexed and uncomplexed halogen containing compounds, as previously described. The water 210 and/or water-base solution 212 is contacted with mixture 206, after which separation of a water-comprising phase from an IBU-organic compound phase is achieved by permitting phasing and by subsequently draining the water-comprising phase 214 as previously described. The IBU-organic compound phase 216 may then be filtered at step 218 to remove suspended solids.

The water-washed, filtered IBU-comprising mixture 220 then passes to a heat treatment step 222. After any light end organics (typically solvents) 224 are flashed off, the resulting residue is heat treated at temperatures ranging from about 130° C. to about 350° C., under an inert atmosphere such as nitrogen, for a time period ranging from about 0.01 hour to about 8 hours. The heat treated material 226 is then cooled to a temperature ranging from about 70° C. to about 160° C.

A solvent(s) 228 is then added to heat treated material 226 to produce a solution 232 from which the ibuprofen-comprising mixture 226 can be crystallized. This solvent can be added at points 228 or 231 or a combination thereof. A filtration step 230 may be used to remove entrapped solids from solution. The heat-treated, filtered mixture 232 is then further processed in crystallization step 234 in the manner described regarding FIG. 1 and FIG. 2 crystallizations, to provide a slurry 236 containing IBU crystals.

Crystallization slurry 236 is then filtered cold in step 238 as previously described. The first mother liquor from filtering step 238 is typically sent solvent recovery step 244 from which solvents 246 are recovered and heavy ends/residue 248 is obtained. A solvent 240 can be used to clean the crystals on the filter. The wash solvent 250 recovered from the cleaning step, can be recycled into the process, typically wash solvent 250 is fed back into the process at solvent addition points 204, 228, and 231. The IBU solids 252 resulting from filtration step 238 can then be dried in drying step 254 or can be remelted and further processed for purification.

Typically drying 254 is conducted over the temperature range necessary to remove hydrocarbon solvent(s) 256. The temperature and pressure conditions used for drying have been previously described. Hydrocarbon solvents 256 can be recycled to solvent addition points such as 204, 228, 231, and 240. Dried IBU product 258 meets the product specification requirements previously described.

Example 3 below is a specific example of a laboratory execution of the process shown schematically in FIG. 3, and described above.

EXAMPLE 3

A 700 gm sample of crude ibuprofen was melted, combined with 554 gm of warm hexane (56 wt/wt %), heated to 60° C. and washed with 1050 ml of deionized water at 60° C. in the manner previously described. The water layer was decanted and the pH of the water layer was determined. The water washing step was repeated (usually two to three times) until the pH of decanted water layer was equal to or greater than 2.9. If suspended solids were noticed in the resulting hexane layer, the solution was filtered to remove such solids.

After the hexane was removed in a flashing step, the resulting residue was heat treated at 230° C. for three hours under a nitrogen atmosphere. The resulting material was cooled to 140° C. and filtered.

The heat-treated material from the preceding step was combined with sufficient warm hexane to prepare a 40 wt/wt % solution and was heated to 60° C. If the heat-treated residue is colored, the heated 40% solution can be treated with carbon, e.g. 5 gms carbon per 100 gms ibuprofen charged, and filtered. Such a carbon treatment has been shown to reduce coloration. Otherwise, the heated 40% solution was cooled rapidly to 25° C. and held at this temperature for one hour and then cooled to 5° C., thus affording a white crystallization slurry ready for filtration.

The crystallization slurry generated in the preceding step was filtered cold under vacuum as previously described in Example 2. The resulting solids were washed with 1040 ml of 0°–5° C. hexane. In a production method, the mother liquor and wash liquor can be recycled to minimize ibuprofen and solvent losses.

The filtered and washed solids obtained in the previous step were dried at about 50° C., under 2–49 mm Hg vacuum overnight. The solids thus obtained were analyzed to be as follows:

| Analysis | |
|---|---|
| Ibuprofen Assay | 100.0% |
| Organic Impurities (HPLC) | 0.33% |
| Total TPP + TPPO | 0.70 ppm |
| Palladium | <2 ppm |
| Chloride | <8 ppm |

Figure 4:
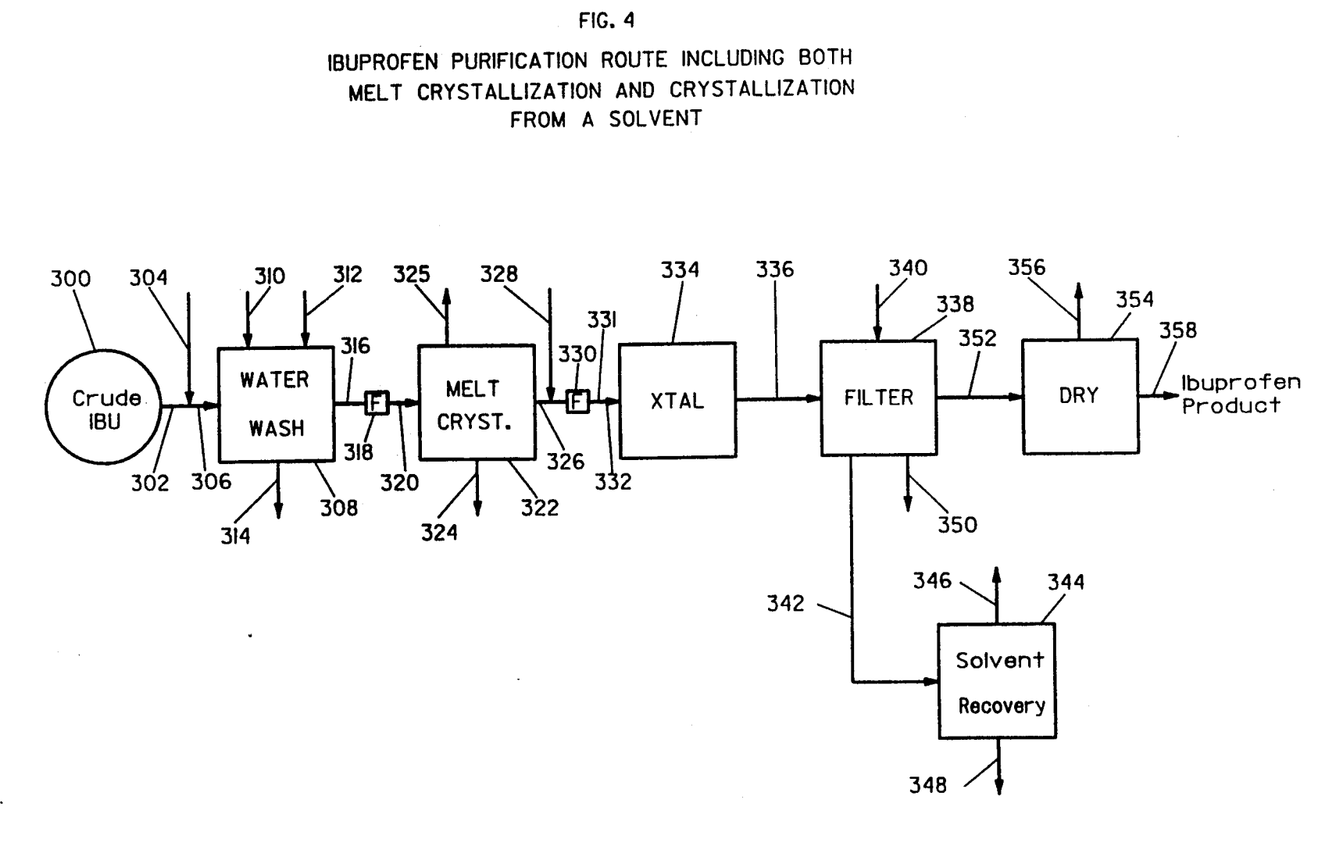
FIG. 4 shows a schematic which includes melt crystallization in place of the heat treatment shown in FIG. 3.

FIG. 4 shows a schematic wherein crude ibuprofen-comprising reaction mixture (crude IBU) 300 is water washed 308 at least once to remove complexed and uncomplexed halogen-containing compounds, as previously described; is subsequently melt crystallized 322; is then crystallized from a solvent(s) 334 and then dried 354 to produce ibuprofen product 358.

The crude IBU-comprising reaction mixture 300 is melted as previously described, and to melt 302 is added a hydrocarbon solvent(s) 304, to provide a less viscous mixture 306, as described for FIGS. 1 through 3. Mixture 306 is then water washed 308 at least once to remove complexed and uncomplexed halogen-containing compounds, as previously described. The water 310 and/or water-base solution 312 is contacted with mixture 306, after which separation of a water-comprising phase 314 from an IBU-organic compound phase 316 is accomplished as previously described. The IBU-organic compound phase 316 may then be filtered 318 to remove any suspended solids.

The water-washed, filtered IBU-comprising mixture 320 then passes to a melt-crystallization step 322, wherein mixture 320 is vacuum flashed to remove solvent 325. The resulting residue containing the IBU is then charged to a melt crystallization apparatus (such as a static or dynamic melt crystallizer) for purification. Typically the IBU-comprising residue is cooled below its freezing point to produce a crystalline mass from which any liquid residue is drained off at a point such as 324 shown in FIG. 4. Subsequently, the crystalline mass can be slowly reheated, with liquid which results from reheating being drained (at point 324 in FIG. 4) to further purify the reduced crystalline mass remaining after reheating. To the remaining crystalline mass 326 is added a solvent to place these solids 326 into a solution or mixture from which a second crystallization from solvent or mixture 334 can be conducted. The solvent can be added at addition points shown in FIG. 4 at 328 and 331 or can be added at a combination thereof.

Suspended solids may be removed by filtration 330 prior to further processing of the IBU-comprising, melt crystallized solution or mixture 332.

The solution or mixture 332 is further processed in crystallization step 334, in a manner described with reference to previous FIGs., to provide a slurry 336 containing IBU crystals.

Crystallization slurry 336 is then filtered cold as previously described. The first mother liquor from filtering step 338 is typically sent to a solvent recovery step 344, from which solvent(s) 346 are recovered and heavy ends/residue 348 is obtained.

Wash solvent 340 can be used to clean the filtered crystals. The wash solvent 350, resulting after the cleaning step, can be recycled into the process, and is typically fed back into the process at solvent addition points such as 304, 328, and 331.

The IBU solids 352 resulting from filtration step 338 can then be dried in drying step 354 or can be remelted and further processed for purification.

Typically drying 354 is conducted over the temperature range necessary to remove hydrocarbon solvent(s) 356. The temperature and pressure conditions used for drying have been previously described. Hydrocarbon solvents 356 can be recycled to solvent addition points such as 304, 328, 331, and/or 340. Dried IBU product 358 meets the product specification requirements previously described.

Example 4 below is a specific example of a laboratory execution of the process shown schematically in FIG. 4 and described above.

EXAMPLE 4

A 700 gm sample of crude ibuprofen-comprising reaction product mixture was melted, combined with 554 gm of warm heptane (56 wt/wt %), heated to about 70° C. and washed with 1050 ml of deionized water at about 70° C. The water layer was decanted and the pH is determined. The water washing step was usually repeated (two to three times) until the pH of the decanted water layer was equal to or greater than 2.9. If suspended solids were noticed in the resulting heptane layer, the solution was filtered to remove such solids.

The washed heptane solution from the preceding step was vacuum flashed to remove heptane solvent. The resulting residue containing the ibuprofen product was charged to a static melt crystallization apparatus for purification. The following analyses illustrate the effectiveness of this melt crystallization step:

| Analysis | Crude Ibuprofen | Melt-Crystallized Material |
|---|---|---|
| Ibuprofen Assay | 94.8% | 99.5% |
| 3-IBU (*) | 0.3% | ND |
| Other Organic Impurities (GC) | 2.9% | 0.3% |
| Total TPP + TPPO | 5400 ppm | 26 ppm |

(*) 3-IBU is defined as 2-(3'-isobutylphenyl)propionic acid.

The melt-crystallized material from the preceding step was combined with sufficient warm heptane to prepare a 25 wt % solution and heated to 70° C. If suspended solids are noted during dissolution, the mixture was filtered to remove such solids. The heated solution mentioned above was cooled for 30 min. in an ice bath to produce a crystallization slurry.

The crystallization slurry generated in the preceding step, was filtered cold under vacuum to produce ibuprofen crystals and a mother liquor. The resulting ibuprofen crystals were washed with 0° C. heptane (200 ml heptane wash per 100 g of ibuprofen-comprising mixture) to produce washed crystals and wash solvent. In a production mode, the mother liquor and wash solvent can be recycled to minimize ibuprofen loss.

The filtered and washed solids obtained above were dried at about 50° C. under 48 mm Hg vacuum overnight. The solids thus obtained typically had the following analysis:

| Analysis | |
|---|---|
| Ibuprofen Assay | 99.9% |
| Other Organic Impurities (GC) | <0.1% |
| Total TPP + TPPO | <5 ppm |
| Chloride | <10 ppm |

Figure 5:
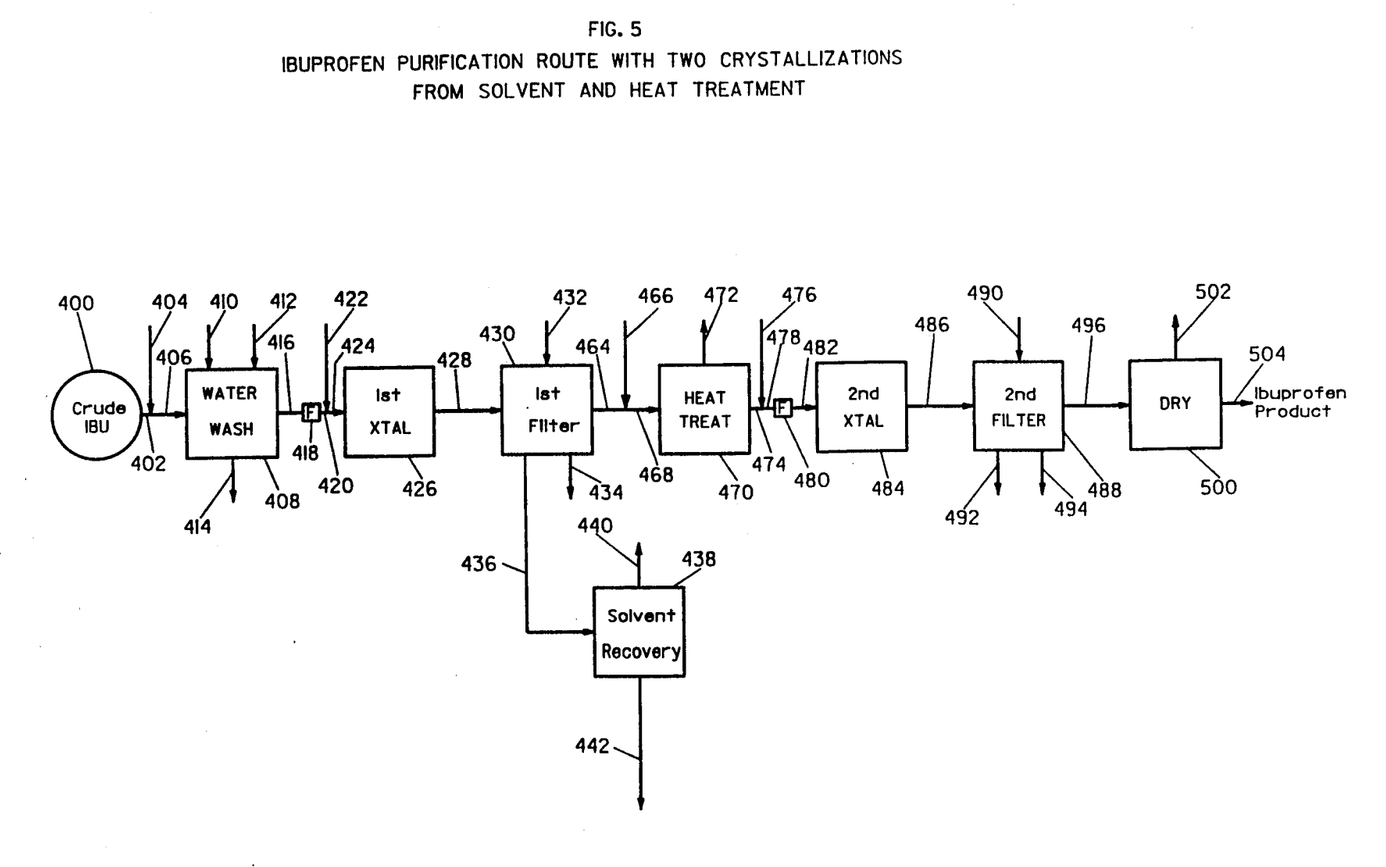
FIG. 5 shows a schematic of a method which provides a product having excellent purity. This method includes at least one water wash, a first crystallization of ibuprofen form hydrocarbon solvent, a heat treatment step, a second crystallization of ibuprofen from hydrocarbon solvent, and a drying step.

FIG. 5 shows a schematic of a purification process wherein the crude IBU-comprising reaction mixture 400 is water washed 408 at least once; is crystallized from a solvent a first time 426; is heat-treated 470; is crystallized from a solvent a second time 484; and is typically dried 500 to remove residual solvent.

The crude IBU-comprising reaction mixture 400 is melted as previously described, and to melt 402 is added a hydrocarbon solvent(s) 404, to produce IBU-comprising mixture 406.

Mixture 406 is then water washed 408 at least once to remove complexed and uncomplexed halogen-containing compounds, as previously described. The water 410 and/or water-base solution 412 is contacted with mixture 406, after which separation of a water-comprising phase (wash water) 414 from an IBU-organic compound phase 416 is achieved by permitting phasing and by subsequent draining of wash water 414. The IBU-organic compound phase 416 may then be filtered at step 418 to remove any suspended solids.

The water-washed, filtered, IBU-comprising mixture 420 may then be further diluted with solvent 422 to provide a lower viscosity mixture or solution 424 which can subsequently be used in crystallization step 426.

Mixture or solution 424 is processed in crystallization step 426 in the manner described regarding the previous FIGs., to provide a slurry 428 containing IBU crystals.

Crystallization slurry 428 is then filtered cold 430 as previously described. The first mother liquor 436 from filtering step 430 is typically sent to solvent recovery step 438 from which solvent(s) 440 are recovered and first mother liquor residue 442 is obtained.

Mother liquor residue 442 can be processed in a secondary recovery operation so that the ibuprofen content of residue 442 can be processed through a secondary recovery operation and then recycled back into the FIG. 5 purification route.

Solvent 432 can be used to clean the crystals on the filter in first filter step 430. The wash solvent 434, after the cleaning step, can be recycled into the process, and is typically fed back into the process at solvent addition points 404 and 422.

The IBU-comprising solids 464 resulting from filtration step 430 are then redissolved (to permit easier transportation within the process) by the addition of solvent 466 to produce a solution 468. The solvent, including any highly volatile impurities, is then flashed off 472 prior to heat treatment in heat treatment step 470. The resulting residue (after solvent flashing) is heat treated at temperatures ranging from about 130° C. to about 350° C. under an inert atmosphere, such as a nitrogen atmosphere, for a time period ranging from about 0.01 hour to about 8.0 hours. The inert atmosphere can be used to purge the vapor space of heat treated mixture, thereby assisting in the removal of halogen-comprising compounds and other highly volatile impurities. The heat treated material 474 is then cooled to a temperature ranging from about 70° C. to about 160° C.

A solvent(s) 476 is then typically added to produce a solution 482 from which ibuprofen-comprising mixture 474 can be crystallized. A filtration step 480 may be used to remove entrapped solids from solution 478. The solvent 476 may be added prior to or after such a filtration step. The heat-treated, filtered mixture 482 is then further processed in second crystallization step 484 in the manner described regarding FIG. 1 and FIG. 2 crystallizations.

The rate of cooling in second crystallization step 484 affects the final crystal size obtained, and this cooling rate can be adjusted to provide the size of crystals desired.

Crystallization slurry 486 is then filtered cold in step 488 as previously described. The second mother liquor 492 is typically recycled to points 404 or 422 as shown in FIG. 5. Solvent 490 which is added to wash the crystals on the filter is recovered as wash solvent 494, and can be recycled into the process; typically wash solvent 494 may be fed back into the process at solvent addition points 404, 422, 466, and 476. The IBU solids 496 resulting from filtration step 488 can then be dried in drying step 500.

Typically drying 500 is conducted over the temperature range necessary to remove hydrocarbon solvent(s) 502. The temperature and pressure conditions used for drying have been previously described. Hydrocarbon solvents 502 may be recycled to solvent addition points 404, 422, 466, 476, and 490. Dried IBU product 504 meets the product specifications previously described.

Example 5 below is a specific example of a laboratory execution of the process shown schematically in FIG. 5, and described above.

EXAMPLE 5

A 700 gm sample of crude ibuprofen was melted, combined with 554 gm of warm hexane (56 wt/wt %), heated to 60° C. and washed with 1,050 ml of deionized water at 60° C. Subsequently, the crude ibuprofen melted mixture was washed at 60° C. using about 260 ml of deionized water containing about 3,000 ppm of sodium hydroxide. After two water-sodium hydroxide washes, a final water wash using 1,050 ml of deionized water was conducted. The final water wash layer was decanted and the pH was determined to be 5.3. Care must be taken that the final water wash pH does not significantly exceed about 5.7 since the sodium hydroxide can form a surface active agent with ibuprofen, thereby causing emulsion problems. If suspended solids were noticed in the resulting hexane layer, the solution was filtered to remove such solids.

After the last traces of wash water were decanted from the preceding step, another 1,079 gm portion of warm hexane was added to adjust the ibuprofen concentration to about 30 wt %. The temperature was adjusted back to 60° C. The solution was next cooled to and held at 25° C. for one hour and then further cooled to 5° C. to produce a crystallization slurry.

The slurry from the preceding step was filtered cold under vacuum, thus affording solids and mother liquor solution. The resulting solids were washed with 1,400 ml of 5° C. hexane while the mother liquor was fed to a hexane recovery column for solvent recovery by distillation. In a production mode, the mother liquor residue after distillation and solvent recovered, as well as wash solvent can be recycled to prevent ibuprofen loss.

The solids from the filtration step described above were transferred to a heat treatment flask and heated to 180° C. for one hour with stirring under a nitrogen atmosphere. The heat-treated melt was cooled to 140° C. and filtered to remove suspended and precipitated solids.

The heat-treated material from the preceding step was next combined with sufficient warm hexane to prepare a 40 wt % solution and heated to 60° C. This solution was cooled to 5° C. over the next 6-8 hours to produce a crystallization slurry.

The crystallization slurry generated in the preceding step was filtered cold under vacuum. The resulting solids were washed with 5° C. hexane. The second mother liquor and wash solvent can be recycled to minimize ibuprofen loss.

The filtered solids thus obtained in the previous step were dried at about 50° C. under 49 mm Hg vacuum overnight. The solids thus obtained were sent in for analysis:

| Analysis | |
|---|---|
| Ibuprofen Assay | 99.9% |
| Other Organic Impurities (HPLC) | 0.29% |
| Total TPP + TPPO | 0.72 ppm |
| Palladium | <2 ppm |
| Chloride | <5 ppm |
| Particle Size | 20-60 micron |

EXAMPLE 6

Secondary Recovery of Ibuprofen from First Mother Liquor

During the discussion regarding FIG. 5, it was submitted that mother liquor residue 442 can be processed in a secondary recovery operation so that the ibuprofen content of residue 442 can be recycled back into the FIG. 5 purification route. The secondary recovery can be carried out using crystallization from a solvent, melt crystallization, distillation, or a combination thereof. The more likely techniques for secondary processing of the mother liquor residue are crystallization from a solvent or distillation; both techniques are described below.

Process of First Mother Liquor Prior to SEcondary Recovery (For Purposes of Removing Excess Solvent)

A 3,727 gm sample of first mother liquor from a purification scheme involving two stages of crystallization (with no heat treatment, see FIG. 1) was distilled by placing a flask containing the mother liquor in an 80° C. bath, while subjecting the flask to 49 mm Hg vacuum; the principal distillate removed was excess hexane solvent. This distillation afforded a 430 gm sample of mother liquor residue containing 36.4% ibuprofen, 18.9% hexane, 756 ppm TPP+TPPO and the remainder other organic and inorganic impurities.

Secondary Recovery of Ibuprofen Involving Crystallization

The residue sample generated above was cooled to 12° C. whereby the resulting crystals were filtered and washed with 400 ml of 10° C. hexane thus affording 87.2 gms of recovered ibuprofen.

Purification of Recovered Ibuprofen. The recovered material was purified with the "Basic Purification Route without Heat Treatment" (see FIG. 1), as described above thus affording a satisfactory final purified ibuprofen product. Analytical data for the recovered and purified material is presented below.

| | Material | |
|---|---|---|
| Analysis | Secondary Recovery by Crystallization | Further Purified Using FIG. 1 Route |
| Ibuprofen Assay | 92.4% | 99.8% |
| Organic Impurities (HPLC) | 8.51% | 0.04% |
| Total TPP + TPPO | 554 ppm | 2.1 ppm |

Secondary Recovery of Ibuprofen Involving Distillation

In an analogous manner, a sample of first mother liquor residue was distilled under vacuum. After several small light-ends fractions were removed, the ibuprofen-containing fraction was distilled at 175-°180° C. under 10 mm Hg vacuum affording 103 gms of recovered material. This sample was purified satisfactorily using the basic purification route without heat treatment. Analyses of these samples are shown below:

| | Material | |
|---|---|---|
| Analysis | Secondary Recovery by Distillation | Further Purified Using FIG. 1 Route |
| Ibuprofen Assay | 89.5% | 99.8% |
| Organic Impurities (HPLC) | 12.9% | 0.22% |
| Total TPP + TPPO | 224 ppm | 0.37 ppm |

The preferred examples described above are for purposes of illustration of the present invention. One skilled in the art can make modifications and equivalent substitutions which are readily apparent in view of the disclosure herein, which modifications and substitutions produce an equivalent result. Such equivalents are intended to fall within the scope of the present invention as defined in the claims which follow.

We claim:

1. A method of purifying an ibuprofen-comprising first mixture, which mixture comprises at least one complex, said complex comprising at least one ibuprofen molecule, said method comprising the steps of:
    (a) treating an ibuprofen-comprisign first mixture by heating said mixture, washing said mixture with a liquid comprising water, azeotroping uncomplexed acid from said mixture, or a combination thereof, thereby destabilizing or breaking up at least one complex comprising at least on ibuprofen molecule; and
    (b) subsequently crystallizing ibuprofen at least once from a second solution or mixture comprising said first ibuprofen-comprising mixture.

2. The method of claim 1 wherein said ibuprofen-compri,sing first mixture comprises halides and phosphorus-containing compounds.

3. The method of claim 1 wherein said ibuprofen-comprising first mixture comprises a metallic reaction catalyst.

4. The method of claim 1 wherein said ibuprofen-comprising first mixture comprises halides, phosphorus-containing compounds and a metallic reaction catalyst.

5. The method of claim 3 wherein said metallic reaction catalyst comprises palladium.

6. The method of claim 1, claim 2, claim 3, or claim 4 wherein said at least one complex comprising at least one ibuprofen molecule is destabilized or broken up using at least one water wash treatment.

7. The method of claim 1, claim 2, claim 3 or claim 4, wherein said at least one complex is destabilized or broken up using at least one heat treatment.

8. The method of claim 1, claim 2, claim 3, or claim 4, wherein said at least one complex is destabilized or broken up using a combination of at least one water wash and at least one heat treatment.

9. The method of claim 6 wherein said at least one water wash comprises a water wash with a base present in at least one instance.

10. The method of claim 8 wherein said at least one water wash comprises a water wash with a base present in at least one instance.

11. The method of claim 1, claim 2, or claim 4, wherein said complex is destabilized or broken up by azeotroping off substantial amounts of uncomplexed acid present in said ibuprofen-comprising first mixture.

12. The method of claim 6 including an additional step wherein solvent residue remaining on the crystallized ibuprofen is removed using a drying step.

13. The method of claim 7 including an additional step wherein solvent residue remaining on the crystallized ibuprofen is removed using a drying step.

14. The method of claim 8 including an additional step wherein solvent residue remaining on the crystallized ibuprofen is removed using a drying step.

15. The method of claim 7 wherein said at least one heat treating step comprises a distillation, and wherein said ibuprofen is removed as a distillate fraction.

16. A method of purification of an ibuprofen-comprising first mixture, which first mixture comprises halides and phosphorus-containing compounds, said method comprising the steps of:
    (a) washing the ibuprofen-containing first mixture, using at least one water washing step;
    (b) melt crystallizing the washed ibuprofen-comprising first mixture at least once to produce an ibuprofen-comprising second solution or mixture; and,
    (c) crystallizing ibuprofen at least once from a third solution or mixture comprsiing the melt crystallized second solution or mixture, and including at least one solvent from which ibuprofen is crystallized.

17. The method of claim 16 including an additional step wherein solvent residue remaining on the crystallized ibuprofen is removed using a drying step.

18. A method of purification an ibuprofen-comprising first mixture, which first mixture comprises halides and phosphorus-containing compounds, said method comprsiing the steps of:
    (a) washing an ibuprofen-comprising first mixture using at least one water washing step;
    (b) first crystallizing ibuprofen from a second solution or mixture comprising said washed first mixture, and includign at least one hydrocarbon solvent from which said ibuprofen is crystallized;
    (c) heating treating said first crystallized ibuprofen at a temperature sufficient to cause the destabilization or breaking up of a complex which includes a halogen-phosphorus-containing compound and at least oen ibuprofen molecule, whereby the destabilization products of such complex can be separated from said ibuprofen molecule; and
    (d) second crystallizing ibuprofen from a third solution or mixture comprising said heat-treated, first-crystalized ibuprofen mixture, and including at least one hydrocarbon solvent from which said ibuprofen is crystallized.

19. The method of claim 18 includign an additional step wherein solvent residue remaining on the crystallized ibuprofen is removed using a drying step.

20. A method of purification of an ibuprofen-comprising first mixture, which first mixture comprises a metallic reaction catalyst, said method comprising the steps of:
  (a) washing an ibuprofen-comprising first mixture using at least one water washing step;
  (b) first crystallizing ibuprofen from a second solution or mixture comprising said washed first mixture, and including at least one hydrocarbon solvent from which said ibuprofen is crystallized;
  (c) heat treating said first crystallized ibuprofen at a temperature sufficient to cause destabilization or breaking up of a complex which includes a metallic compound and at least one ibuprofen molecule, whereby the destabilization products of such complex can be separated from said ibuprofen molecule; and
  (d) second crystallizing ibuprofen from a third solution or mixture comprising said heat-treated, first-crystallized ibuprofen mixture, and including at least one hydrocarbon solvent from which said ibuprofen is crystallized.

21. The method of claim 20 including an additional step wherein solvent residue remaining on the crystallized ibuprofen is removed using a drying step.

* * * * *

UNITED STATES PATENT AND TRADEMARK OFFICE
CERTIFICATE OF CORRECTION

PATENT NO. : 5,151,551
DATED : September 29, 1992
INVENTOR(S) : Edward G. Zey, Thomas H. Shockley, Debra A. Ryan, & Gary L. Moss It is certified that error appears in the above-indentified patent and that said Letters Patent is hereby corrected as shown below:

| | |
|---|---|
| Column 1, line 55 | Should read, "zone (H+/IBPE) is at least about 0.15; and (3) dissoci-". |
| Column 2, line 15 | Should read, "1-(4-isobutylethylbenzene, 1-(4'-isobutylphenyl)ethyl" |
| Column 13, line 68 | Should read, "comprising reaction mixture (crude IBU)" |
| Column 14, line 41 | Should read, "ing compound, halogen-containing acid, and" |
| Column 23, line 48 | Should read, "complex comprising at least one ibuprofen mole-" |

Signed and Sealed this

Twenty-eighth Day of December, 1993

Attest:

BRUCE LEHMAN

*Attesting Officer*    *Commissioner of Patents and Trademarks*